United States Patent
Choi et al.

(10) Patent No.: US 10,752,579 B2
(45) Date of Patent: Aug. 25, 2020

(54) PRODUCTION METHOD OF CARBAMIC ACID ESTER

(71) Applicant: NATIONAL INSTITUTE OF ADVANCED INDUSTRIAL SCIENCE AND TECHNOLOGY, Ibaraki (JP)

(72) Inventors: Jun-Chul Choi, Ibaraki (JP); Norihisa Fukaya, Ibaraki (JP); Qiao Zhang, Ibaraki (JP); Hiroyuki Yasuda, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 16/328,530

(22) PCT Filed: Aug. 31, 2017

(86) PCT No.: PCT/JP2017/031414
§ 371 (c)(1),
(2) Date: Feb. 26, 2019

(87) PCT Pub. No.: WO2018/043658
PCT Pub. Date: Mar. 8, 2018

(65) Prior Publication Data
US 2019/0185420 A1 Jun. 20, 2019

(30) Foreign Application Priority Data

Sep. 2, 2016 (JP) .................. 2016-172076
Sep. 2, 2016 (JP) .................. 2016-172077

(51) Int. Cl.
C07C 269/04 (2006.01)
C07C 271/28 (2006.01)
C07B 61/00 (2006.01)

(52) U.S. Cl.
CPC .......... *C07C 269/04* (2013.01); *C07C 271/28* (2013.01); *C07B 61/00* (2013.01)

(58) Field of Classification Search
CPC ...... C07B 61/00; C07C 269/04; C07C 271/28
See application file for complete search history.

(56) References Cited

U.S. PATENT DOCUMENTS

2002/0120140 A1   8/2002   Lee
2015/0133676 A1   5/2015   Kim et al.

FOREIGN PATENT DOCUMENTS

| JP | 2002212159 | 7/2002 |
| JP | 2004512316 | 7/2002 |
| JP | 200622043 | 1/2006 |
| JP | 2012250930 | 12/2012 |
| JP | 201593870 | 5/2015 |
| WO | 2015133247 | 9/2015 |

OTHER PUBLICATIONS

Zang et al. (A Simple Zinc Catalyst for Carbamate Synthesis Directly from CO2, ChemSusChem, 10, pp. 1501-1508, published Mar. 2017) (Year: 2017).*
Germain et al. (Synthesis of carbamates from carbon dioxide promoted by organostannanes and alkoxysilanes, Applied Organometallic Chemistry, p. 1-10, Published Jan. 2017) (Year: 2017).*
Zhang et al. "A Simple Zinc Catalyst for Carbamate Synthesis Directly from CO2", ChemSusChem, 10:1501-1508 (2017).
International Search Report and Written Opinion with English language translation of the International Search Report corresponding to International Application No. PCT/JP2017/031414, dated Nov. 27, 2017, 33 pages.

* cited by examiner

*Primary Examiner* — Yevgeny Valenrod
*Assistant Examiner* — Blaine G Doletski
(74) *Attorney, Agent, or Firm* — Myers Bigel, P.A.

(57) ABSTRACT

A method of production of carbamic acid ester has a high yield and high selectivity and is superior in economy. The method of production of a carbamic acid ester includes reacting an amine, carbon dioxide, and an alkoxysilane compound in the presence of a catalyst containing a zinc compound or an alkali metal compound or in the presence of an ionic liquid. A carbamic acid ester is produced, for example by reacting aniline, carbon dioxide, and tetramethoxysilane at a temperature of 150 to 180° C. in the presence of zinc acetate and 2,2'-bipyridine.

17 Claims, No Drawings

PRODUCTION METHOD OF CARBAMIC ACID ESTER

RELATED APPLICATION

This application is a 35 U.S.C. § 371 national phase application of International Application Serial No. PCT/JP2017/031414, filed on Aug. 31, 2017, which claims the benefit, under 35 U.S.C. § 119 (a) of Japanese Patent Application No. 2016-172076, filed on Sep. 2, 2016, and Japanese Patent Application No. 2016-172077, filed on Sep. 2, 2016, the entire contents of each of which are incorporated by reference herein.

TECHNICAL FIELD

The present invention relates to a method of production of a carbamic acid ester including reacting an amine, carbon dioxide, and an alkoxysilane compound.

BACKGROUND ART

Polyurethanes are a representative general-purpose polymer used for housing and building materials, automobile parts, coating materials, and the like. Polyurethanes are produced by reacting a polyfunctional isocyanate with a polyfunctional alcohol. Isocyanates are obtained by thermally decomposing a carbamic acid ester. As a synthesis method of a carbamic acid ester, a method including reacting an amine, carbon dioxide, and a tin alkoxide compound is known (Patent Literature 1).

According to the method described in Patent Literature 1, a carbamic acid ester can be synthesized with a high yield and high selectivity. Further, the tin alkoxide compound having been used in the reaction can be reused. Therefore, the production method of a carbamic acid ester described in Patent Literature 1 is excellent. However, since a tin alkoxide compound is highly toxic and expensive, the advent of a synthesis method of a carbamic acid ester using a less expensive substance is desired.

CITATION LIST

Patent Literature

Patent Literature 1: International Publication No. WO 2015/133247

SUMMARY OF INVENTION

Technical Problem

The present invention has been made in view of such circumstances, and an object thereof is to provide a method capable of producing a carbamic acid ester with a high yield and high selectivity and is superior in economy.

Solution to Problem

A production method of a carbamic acid ester according to a first aspect of the present invention includes reacting an amine, carbon dioxide, and an alkoxysilane compound in the presence of a catalyst containing a zinc compound. A production method of a carbamic acid ester according to a second aspect of the present invention includes reacting an amine, carbon dioxide, and an alkoxysilane compound in the presence of an ionic liquid. A production method of a carbamic acid ester according to a third aspect of the present invention includes reacting an amine, carbon dioxide, and an alkoxysilane compound in the presence of a catalyst containing an alkali metal compound.

Advantageous Effects of Invention

According to the present invention, a carbamic acid ester is produced with a high yield and high selectivity and is superior in economy.

DESCRIPTION OF EMBODIMENTS

A production method of a carbamic acid ester according to the present invention will be described based on each embodiment and Example. In the second embodiment, duplicated descriptions in the first embodiment are appropriately omitted. In the third embodiment, descriptions overlapping with the first embodiment or the second embodiment are appropriately omitted. Note that when "to" is between two numerical values to represent a numerical range, these two numerical values are also included in the numerical range.

A production method of a carbamic acid ester according to a first embodiment of the present invention includes reacting an amine, carbon dioxide, and an alkoxysilane compound in the presence of a catalyst containing a zinc compound. When the alkoxysilane compound is directly used instead of the tin alkoxide compound or the titanium alkoxide compound used in the production method of a carbamic acid ester described in Patent Literature 1, a carbamic acid ester is difficult to obtain. However, a carbamic acid ester is obtained with a high yield and high selectivity by using the catalyst containing a zinc compound in combination with the alkoxysilane compound.

The zinc compound is preferably at least one of zinc oxide ($ZnO_2$), a zinc halide such as zinc chloride ($ZnCl_2$) and zinc bromide ($ZnBr_2$), zinc trifluoromethanesulfonate ($Zn(OTf)_2$), and zinc acetate ($Zn(OAc)_2$). Zinc acetate is preferable among them. This is because a carbamic acid ester is obtained with high a yield and high selectivity. The catalyst may include a ligand. There is no particular restriction on the ligand as long as the ligand is a compound which forms a coordinate bond with zinc to form a zinc complex. At least one of 1,10-phenanthroline (phen), 2,2'-bipyridine (bpy), N,N'-bis(2-pyridylmethyl)ethylenediamine (bispicen), 1,4,8,11-tetraazacyclotetradecane (cyclam), and ethylenediaminetetraacetic acid (EDTA) represented by the following chemical formulas may be used as the ligand.

[Formula 1]

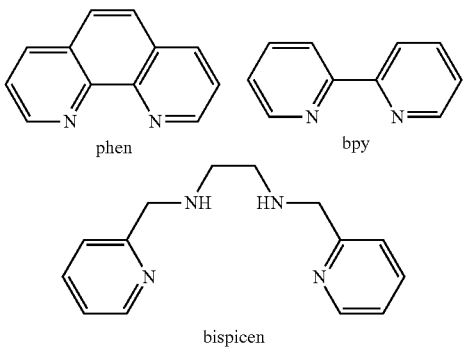

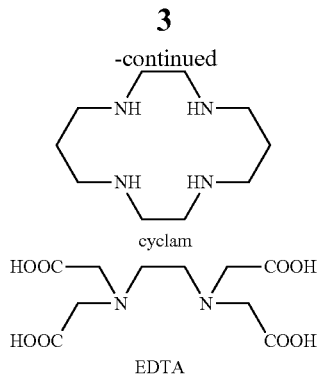

cyclam

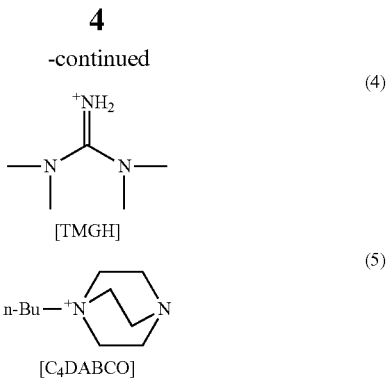

[TMGH]

n-Bu—⁺N⌒N

[C₄DABCO]

A catalyst including zinc acetate as the zinc compound and including at least one of 1,10-phenanthroline, 2,2'-bipyridine, N,N'-bis(2-pyridylmethyl)ethylenediamine, and 1,4,8,11-tetraazacyclotetradecane as the ligand is more preferable. This is because a carbamic acid ester is obtained with an especially high yield and high selectivity.

A production method of a carbamic acid ester according to a second embodiment of the present invention includes reacting an amine, carbon dioxide, and an alkoxysilane compound in the presence of an ionic liquid. A carbamic acid ester is obtained with a high yield and high selectivity by using the ionic liquid in combination with the alkoxysilane compound. It is considered that the ionic liquid serves as a catalyst.

An anion of the ionic liquid is preferably at least one of an acetate ion ($CH_3COO^-$ ([OAc])), a trifluoroacetate ion ($CF_3COO^-$) and a 2,2,2-trifluoroethanol ion ($CF_3CH_2O^-$). A cation of the ionic liquid is preferably at least one of [DBUH] represented by the following (1), [DBNH] represented by the following formula (2), [TBDH] represented by the following formula (3), [TMGH] represented by the following formula (4), and [C₄DABCO] represented by the following formula (5). This is because a carbamic acid ester is obtained with a high yield and high selectivity.

[Formula 2]

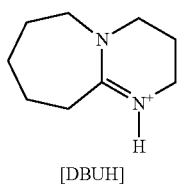

[DBUH]

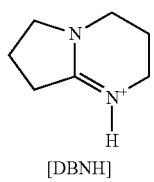

[DBNH]

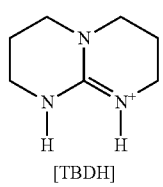

[TBDH]

Among them, an ionic liquid in which the cation is at least one of [DBUH] and [DBNH] and the anion is an acetate ion is more preferable. This is because a carbamic acid ester is obtained with an especially high yield and high selectivity.

A production method of a carbamic acid ester according to a third embodiment of the present invention includes reacting an amine, carbon dioxide, and an alkoxysilane compound in the presence of a catalyst containing an alkali metal compound. A carbamic acid ester is obtained with a high yield and high selectivity by using the alkali metal compound in combination with the alkoxysilane compound. It is considered that the alkali metal compound serves as a catalyst.

The alkali metal compound is preferably at least one of a potassium compound, a rubidium compound, and a cesium compound. Rubidium acetate, cesium acetate, rubidium carbonate, cesium carbonate, potassium acetate, potassium carbonate, potassium hydrogen carbonate, potassium hydroxide and potassium tert-butoxide are particularly preferable among them. This is because a carbamic acid ester is obtained with a high yield and high selectivity.

For example, a N-substituted carbamic acid ester is obtained in the production method of a carbamic acid ester according to each embodiment. Examples of the N-substituted carbamic acid ester include aliphatic carbamic acid esters, alicyclic carbamic acid esters, and aromatic carbamic acid esters, and aromatic carbamic acid esters are preferable among them. For example, carbamic acid monoesters or carbamic acid diesters are obtained in the production method of a carbamic acid ester according to each embodiment. Production of carbamic acid diesters, especially aromatic carbamic acid diesters is useful for industry.

Examples of a carbamic acid ester obtained by the production method according to each embodiment include methyl N-butylcarbamate, ethyl N-butylcarbamate, propyl N-butylcarbamate, butyl N-butylcarbamate, pentyl N-butylcarbamate, hexyl N-butylcarbamate, cyclohexyl N-butylcarbamate, methyl N-t-butylcarbamate, ethyl N-t-butylcarbamate, propyl N-t-butylcarbamate, butyl N-t-butylcarbamate, pentyl N-t-butylcarbamate, hexyl N-t-butylcarbamate, cyclohexyl N-t-butylcarbamate, methyl N-pentylcarbamate, ethyl N-pentylcarbamate, propyl N-pentylcarbamate, butyl N-pentylcarbamate, pentyl N-pentylcarbamate, hexyl N-pentylcarbamate, cyclohexyl N-pentylcarbamate, methyl N-hexylcarbamate, ethyl N-hexyl carbamate, propyl N-hexylcarbamate, butyl N-hexylcarbamate, pentyl N-hexylcarbamate, hexyl N-hexylcarbamate, cyclohexyl N-hexylcarbamate, methyl N-cyclohexylcarbamate, ethyl N-cyclohexylcarbamate, propyl N-cyclohexylcarbamate, butyl N-cyclohexylcarbamate, pentyl N-cyclohexylcarbamate, hexyl N-cyclohexylcarbamate, cyclohexyl N-cyclohexylcarbamate, methyl N-phenylcarbamate ethyl N-phenylcarbamate, propyl N-phenylcarbamate, butyl N-phenylcarbamate, pentyl N-phenylcarbamate, hexyl N-phenylcarbamate, cyclohexyl N-phenylcarbamate, methyl N-tolylcarbamate (all isomers), ethyl N-tolylcarbamate (all isomers), propyl N-tolylcarbamate (all isomers), butyl N-tolylcarbamate (all isomers), pentyl N-tolylcarbamate (all isomers), hexyl N-tolylcarbamate (all isomers), cyclohexyl N-phenylcarbamate (all isomers), methyl N-(fluorophenyl)carbamate (all isomers), ethyl N-(fluorophenyl)carbamate (all isomers), propyl N-(fluorophenyl)carbamate (all isomers), butyl N-(fluorophenyl)carbamate (all isomers), pentyl N-(fluorophenyl)carbamate (all isomers), hexyl N-(fluorophenyl)carbamate (all isomers), cyclohexyl N-(fluorophenyl)carbamate (all isomers), methyl N-(chlorophenyl)carbamate (all isomers), ethyl N-(chlorophenyl)carbamate (all isomers), propyl N-(chlorophenyl)carbamate (all isomers), butyl N-(chlorophenyl)carbamate (all isomers), pentyl N-(chlorophenyl)carbamate (all isomers), hexyl N-(chlorophenyl)carbamate (all isomers), cyclohexyl N-(bromophenyl)carbamate (all isomers), methyl N-(bromophenyl)carbamate (all isomers), ethyl N-(bromophenyl)carbamate (all isomers), propyl N-(bromophenyl)carbamate (all isomers), butyl N-(bromophenyl)carbamate (all isomers), pentyl N-(bromophenyl)carbamate (all isomers), hexyl N-(bromophenyl)carbamate (all isomers), cyclohexyl N-(bromophenyl)carbamate (all isomers), methyl N-(iodophenyl)carbamate (all isomers), ethyl N-(iodophenyl)carbamate (all isomers), propyl N-(iodophenyl)carbamate (all isomers), butyl N-(iodophenyl)carbamate (all isomers), pentyl N-(iodophenyl)carbamate (all isomers), hexyl N-(iodophenyl)carbamate (all isomers), cyclohexyl N-(iodophenyl)carbamate (all isomers), methyl N-(nitrophenyl)carbamate (all isomers), ethyl N-(nitrophenyl)carbamate (all isomers), propyl N-(nitrophenyl)carbamate (all isomers), butyl N-(nitrophenyl)carbamate (all isomers), pentyl N-(nitrophenyl)carbamate (all isomers), hexyl N-(nitrophenyl)carbamate (all isomers), cyclohexyl N-(nitrophenyl)carbamate (all isomers), methyl N-(trifluoromethylphenyl)carbamate (all isomers), ethyl N-(trifluoromethylphenyl)carbamate (all isomers), propyl N-(trifluoromethylphenyl)carbamate (all isomers), butyl N-(trifluoromethylphenyl)carbamate (all isomers), pentyl N-(trifluoromethylphenyl)carbamate (all isomers), hexyl N-(trifluoromethylphenyl)carbamate (all isomers), cyclohexyl N-(trifluoromethylphenyl)carbamate (all isomers), methyl N-(methoxyphenyl)carbamate (all isomers), ethyl N-(methoxyphenyl)carbamate (all isomers), propyl N-(methoxyphenyl)carbamate (all isomers), butyl N-(methoxyphenyl)carbamate (all isomers), pentyl N-(methoxyphenyl)carbamate (all isomers), hexyl N-(methoxyphenyl)carbamate (all isomers), cyclohexyl N-(methoxyphenyl)carbamate (all isomers), N,N'-hexanediyl-dicarbamic acid-dimethyl ester, N,N'-hexanediyl-dicarbamic acid-diethyl ester, N,N'-hexanediyl-dicarbamic acid-dibutyl ester (all isomers), N,N'-hexanediyl-dicarbamic acid-dipentyl ester (all isomers), N,N'-hexanediyl-dicarbamic acid-dihexyl ester (all isomers), N,N'-hexanediyl-dicarbamic acid-dicyclohexyl ester, dimethyl-4,4'-methylene-dicyclohexyl carbamate, diethyl-4,4'-methylene-dicyclohexyl carbamate, dipropyl-4,4'-methylene-dicyclohexyl carbamate (all isomers), dibutyl-4,4'-methylene-dicyclohexyl carbamate (all isomers), dipentyl-4,4'-methylene-dicyclohexyl carbamate (all isomers), dihexyl-4,4'-methylene-dicyclohexyl carbamate (all isomers), dicyclohexyl-4,4'-methylene-dicyclohexyl carbamate isomers), 3-(methoxycarbonylamino-methyl)-3,5,5-trimethylcyclohexyl carbamic acid methyl ester, 3-(ethoxycarbonylamino-methyl)-3,5,5-trimethylcyclohexyl carbamic acid ethyl ester, 3-(propyloxycarbonylamino-methyl)-3,5,5-trimethylcyclohexyl carbamic acid propyl ester (all isomers), 3-(butyloxycarbonylamino-methyl)-3,5,5-trimethylcyclohexyl carbamic acid butyl ester (all isomers), 3-(pentyloxycarbonylamino-methyl)-3,5,5-trimethylcyclohexyl carbamic acid pentyl ester (all isomers), 3-(hexyloxycarbonylamino-methyl)-3,5,5-trimethylcyclohexyl carbamic acid hexyl ester (all isomers), 3-(octyloxycarbonylamino-methyl)-3,5,5-trimethylcyclohexyl carbamic acid cyclohexyl ester (all isomers), toluene-dicarbamic acid-dimethyl ester (all isomers), toluene-dicarbamic acid-diethyl ester (all isomers), toluene-dicarbamic acid-dipropyl ester (all isomers), toluene-dicarbamic acid-dibutyl ester (all isomers), toluene-dicarbamic acid-dipentyl ester (all isomers), toluene-dicarbamic acid-dihexyl ester (all isomers), toluene-dicarbamic acid-dicyclohexyl ester (all isomers), N,N'-(4,4'-methanediyl-diphenyl)-dicarbamic acid-dimethyl ester, N,N'-(4,4'-methanediyl-diphenyl)-dicarbamic acid-diethyl ester, N,N'-(4,4'-methanediyl-diphenyl)-dicarbamic acid-dipropyl ester, N,N'-(4,4'-methanediyl-diphenyl)-dicarbamic acid-dibutyl ester, N,N'-(4,4'-methanediyl-diphenyl)-dicarbamic acid-dipentyl ester, N,N'-(4,4'-methanediyl-diphenyl)-dicarbamic acid-dihexyl ester, N,N'-(4,4'-methanediyl-diphenyl)-dicarbamic acid-dicyclohexyl ester, and the like.

The amine used for the production method of a carbonic acid ester according to each embodiment is preferably an aliphatic amine, an alicyclic amine, or an aromatic amine, and an aromatic amine is more preferable among them. Moreover, the amine used for the production method of a carbamic acid ester according to each embodiment is preferably a primary amine or a secondary amine, and a primary amine is more preferable among them. Moreover, the amine used for the production method of a carbamic acid ester according to each embodiment is preferably a monoamine or a diamine. Diamines, especially aromatic diamines, are useful for industry. Examples of the amine used for the production method of a carbamic acid ester according to each embodiment include methylamine, ethylamine, propylamine, isopropylamine, butylamine, t-butylamine, cyclohexylamine, dimethylamine, diethylamine, aniline, aminotoluene (all isomers), dimethylaniline (all isomers), diethylaniline (all isomers), dipropylaniline (all isomers), aminonaphthalene (all isomers), aminomethylnaphthalene (all isomers), dimethylnaphtylamine (all isomers), trimethylnaphtylamine (all isomers), diaminobenzene (all isomers), diaminotoluene (all isomers), methylenedianiline (all isomers), diaminomesitylene (all isomers), diaminobiphenyl (all isomers), diaminodibenzyl (all isomers), bis(aminophenyl)propane (all isomers), bis(aminophenyl)ether (all isomers), bis(aminophenoxyethane) (all isomers), diaminoxylene (all isomers), diaminoanisole (all isomers), diaminophenetole (all isomers), diaminonaphthalene (all isomers), diamino-methylbenzene (all isomers), diamino-methylpyridine (all isomers), diamino-methylnaphthalene (all isomers), ethylenediamine, diaminopropane (all isomers), diaminobutane (all isomers), diaminopentane (all isomers), diaminohexane (all isomers), diaminodecane (all isomers), triaminohexane (all isomers), triaminononane (all isomers), triaminodecane isomers), diaminocyclobutane (all isomers), diaminocyclohexane (all isomers), 3-aminomethyl-3,5,5-trimethylcyclohexylamine (cis isomer and/or trans isomer), methylenebis(cyclohexylamine) (all isomers), and the like.

Examples of the alkoxysilane compound include tetraalkoxysilanes, trialkoxysilanes, dialkoxysilanes, alkoxysilanes, and the like. Tetraalkoxysilanes are preferable among them. Examples of the tetraalkoxysilanes include tetramethoxysilane, tetraethoxysilane, tetra-n-propoxysilane, tetra-iso-propoxysilane, tetraphenoxysilane, and the like. Tetramethoxysilane is preferable among them.

Examples of the trialkoxysilanes include methyltrimethoxysilane, methyltriethoxysilane, methyltri-n-propoxysilane, methyltriisopropoxysilane, methyltriphenoxysilane, ethyltrimethoxysilane, ethyltriethoxysilane, ethyltri-n-propoxysilane, ethyltriisopropoxysilane, ethyltriphenoxysilane, n-propyltrimethoxysilane, n-propyltriethoxysilane, n-propyltri-n-propoxysilane, n-propyltriisopropoxysilane, n-propyltriphenoxysilane, isopropyltrimethoxysilane, isopropyltriethoxysilane, isopropyltri-n-propoxysilane, isopropyltriisopropoxysilane, isopropyltriphenoxysilane phenyltrimethoxysilane, phenyltriethoxysilane, phenyltri-n-propoxysilane, phenyltriisopropoxysilane, phenyltriphenoxysilane, and the like.

Examples of the dialkoxysilanes include dimethyldimethoxysilane, dimethyldiethoxysilane, dimethyldi-n-propoxysilane, dimethyldiisopropoxysilane, dimethyldiphenoxysilane, diethyldimethoxysilane, diethyldiethoxysilane, diethyldi-n-propoxysilane, diethyldiisopropoxysilane, diethyldiphenoxysilane, di-n-propyldimethoxysilane, di-n-propyldiethoxysilane, di-n-propyldi-n-propoxysilane, di-n-propyldiisopropoxysilane, di-n-propyldi-phenoxysilane, diisopropyldimethoxysilane, diisopropyldiethoxysilane, diisopropyldi-n-propoxysilane, diisopropyldiisopropoxysilane, diisopropyldiphenoxysilane, diphenyldimethoxysilane, diphenyldiethoxysilane, diphenyldi-n-propoxysilane, diphenyldiisopropoxysilane, diphenyldiphenoxysilane, and the like.

Examples of the alkoxysilanes include trimethylmethoxysilane, trimethylethoxysilane, trimethyl-n-propoxysilane, trimethylisopropoxysilane, trimethylphenoxysilane, triethylmethoxysilane, triethylethoxysilane, triethyl-n-propoxysilane, triethylisopropoxysilane, triethylphenoxysilane, tri-n-propylmethoxysilane, tri-n-propylethoxysilane, tri-n-propyl-n-propoxysilane, tri-n-propylisopropoxysilane, tri-n-propyl-phenoxysilane, triisopropylmethoxysilane, triisopropylethoxysilane, triisopropyl-n-propoxysilane, triisopropylisopropoxysilane, triisopropylphenoxysilane, triphenylmethoxysilane, triphenylethoxysilane, triphenyl-n-propoxysilane, triphenylisopropoxysilane, triphenylphenoxysilane, dimethylmethoxysilane, dimethylethoxysilane, dimethyl-n-propoxysilane, dimethylisopropoxysilane, dimethylphenoxysilane, diethylmethoxysilane, diethylethoxysilane, diethyl-n-propoxysilane, diethylisopropoxysilane, diethylphenoxysilane, di-n-propylmethoxysilane di-n-propylethoxysilane, di-n-propyl-n-propoxysilane, di-n-propylisopropoxysilane, di-n-propylphenoxysilane, diisopropylmethoxysilane, diisopropylethoxysilane, diisopropyl-n-propoxysilane, diisopropylisopropoxysilane, diisopropylphenoxysilane, diphenylmethoxysilane, diphenylethoxysilane, diphenyl-n-propoxysilane, diphenylisopropoxysilane, diphenylphenoxysilane, and the like.

The method of production according to each embodiment may be performed, for example by filling a reaction container in which the catalyst or the ionic liquid, the amine, and the alkoxysilane compound are present with carbon dioxide, but there is no particular restriction thereon. The reaction temperature at the time of reacting the amine, carbon dioxide, and the alkoxysilane compound is preferably 100 to 200° C., more preferably 120 to 180° C., even more preferably 150 to 180° C. from the viewpoint of sufficiently progressing the reaction and suppressing production of a by-products such as urea, but there is no particular restriction thereon. When the amine, carbon dioxide, and the alkoxysilane compound are reacted at 150 to 180° C., a carbamic acid ester is obtained with a high yield and high selectivity.

The pressure of carbon dioxide at the time of reacting the amine, carbon dioxide, and the alkoxysilane compound in the presence of the catalyst containing the zinc compound is preferably 0.5 to 100 MPa, more preferably 1 to 30 MPa, even more preferably 3 to 20 MPa, but there is no particular restriction thereon. When carbon dioxide at a pressure of 3 to 10 MPa is reacted with the amine and the alkoxysilane compound, a carbamic acid ester is obtained with a high yield and high selectivity.

The pressure of carbon dioxide at the time of reacting the amine, carbon dioxide, and the alkoxysilane compound in the presence of the ionic liquid is preferably 0.1 to 30 MPa, more preferably 1 to 10 MPa, even more preferably 3 to 5 MPa, but there is no particular restriction thereon. When carbon dioxide at a pressure of 1 to 5 MPa is reacted with the amine and the alkoxysilane compound, a carbamic acid ester is obtained with a high yield and high selectivity.

The pressure of carbon dioxide at the time of reacting the amine, carbon dioxide, and the alkoxysilane compound in the presence of the catalyst containing the alkali metal compound is preferably 0.5 to 100 MPa, more preferably 1 to 30 MPa, even more preferably 3 to 20 MPa, but there is no particular restriction thereon. When carbon dioxide at a pressure of 3 to 10 MPa is reacted with the amine and the alkoxysilane compound, a carbamic acid ester is obtained with a high yield and high selectivity.

The reaction time among the amine, carbon dioxide, and the alkoxysilane compound varies according to conditions such as kinds of the catalyst or the ionic liquid, the alkoxysilane compound, and the amine to be used, the reaction temperature, and the pressure of carbon dioxide, but a reaction time of 4 to 24 hours is sufficient. When carbon dioxide and the amine are reacted at 150 to 180° C. for 4 to 24 hours, a carbamic acid ester is obtained with a high yield and high selectivity.

A solvent for the action of the amine, carbon dioxide, and the alkoxysilane compound is not particularly limited as long as the solvent does not hinder production of a carbamic acid ester. The reaction may be solvent-free. Examples of such solvents include hydrocarbons and ethers. Specifically, benzene, toluene, hexane, tetrahydrofuran, diethyl ether, dioxane, acetonitrile, dichloromethane, and the like are exemplified. It is preferable that a solvent other than alcohols be used from the viewpoint of progressing the production reaction of a carbamic acid ester.

EXAMPLES

1. Synthesis of Carbamic Acid Ester Using Zinc Compound Catalyst (Synthesis of Carbamic Acid Ester)

Into an autoclave having an inner volume of 10 mL and equipped with a stirring device, 0.02 mmol of the zinc compound shown in Table 1, the ligand shown in Table 1, 1 mmol of aniline, 2 mmol of tetramethoxysilane, which is the alkoxysilane compound, and 3 mL of acetonitrile, which is the solvent, were charged; a carbon dioxide cylinder was connected to the autoclave; and the autoclave was sealed.

While stirring the inside of the autoclave, the inside of the autoclave was filled with carbon dioxide, the temperature was increased to 150° C., the inner pressure of the autoclave was adjusted so as to be 5 MPa, and the reaction was conducted for 24 hours to synthesize the carbamic acid ester (the following chemical equation). After completion of the reaction, the inside of the autoclave was cooled, and remaining carbon dioxide was released.

[Formula 3]

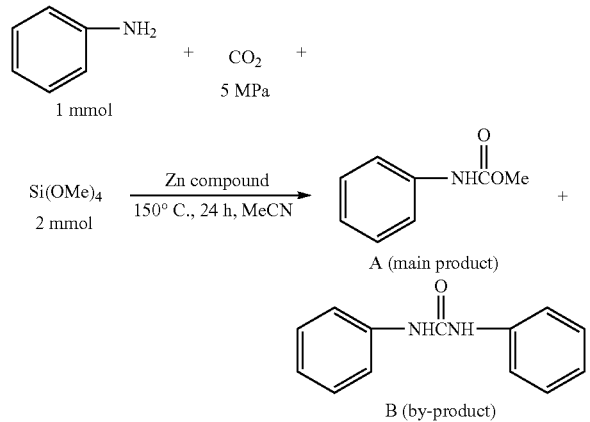

Next, the reaction product was analyzed by liquid chromatography using toluene. Then, respective yields of the main product A and the by-product B were calculated based on aniline. Results thereof are shown in Table 1. Note that Comparative Example 1 was a reaction not using the zinc compound and the ligand. In each Example, the main product A, which was the carbamic acid ester, was obtained with a high yield and high selectivity. On the other hand, very little of the carbamic acid ester was obtained in Comparative Example 1.

TABLE 1

| No. | Zinc compound | Ligand Type | Amount used (mmol) | Yield of A (%) | Yield of B (%) |
|---|---|---|---|---|---|
| Example 1-1 | ZnO | Not used | | 22 | 13 |
| Example 1-2 | ZnCl$_2$ | Not used | | 18 | 9 |
| Example 1-3 | ZnBr$_2$ | Not used | | 29 | 16 |
| Example 1-4 | Zn(OTf)$_2$ | Not used | | 35 | 6 |
| Example 1-5 | Zn(OAc)$_2$ | Not used | | 60 | 6 |
| Example 1-6 | Zn(OAc)$_2$ | phen | 0.06 | 84 | 3 |
| Example 1-7 | Zn(OAc)$_2$ | bpy | 0.06 | 83 | 5 |
| Example 1-8 | Zn(OAc)$_2$ | bispicen | 0.03 | 84 | 5 |
| Example 1-9 | Zn(OAc)$_2$ | cyclam | 0.03 | 60 | 12 |
| Comparative Example 1 | Not used | Not used | | 1 | 2 |

(Dependency of Carbamic Acid Ester Yields on Reaction Temperature and Reaction Time)

Carbamic acid esters were synthesized in the same manner as in Example 1-6, except that reaction temperature and reaction time were changed, and respective yields of the main product A and the by-product B were calculated. Results thereof are shown in Table 2. The main product A, which was the carbamic acid ester, was obtained with yields of 40% or higher over the reaction time of 4 hours or more when the reaction temperature was 150° C. or over the reaction time of 2 hours or more when the reaction temperature was 180° C.

TABLE 2

| No. | Reaction temperature (° C.) | Reaction time (h) | Yield of A (%) | Yield of B (%) |
|---|---|---|---|---|
| Example 1-10 | 120 | 15 | 9 | 8 |
| Example 1-11 | 120 | 24 | 15 | 11 |
| Example 1-12 | 150 | 2 | 21 | 8 |
| Example 1-13 | 150 | 4 | 40 | 9 |
| Example 1-14 | 150 | 7 | 57 | 9 |
| Example 1-15 | 150 | 15 | 84 | 4 |
| Example 1-6 | 150 | 24 | 84 | 3 |
| Example 1-16 | 180 | 2 | 50 | 7 |
| Example 1-17 | 180 | 4 | 85 | 10 |
| Example 1-18 | 180 | 7 | 84 | 3 |
| Example 1-19 | 180 | 15 | 77 | 5 |
| Example 1-20 | 180 | 24 | 70 | 5 |

(Dependency of Carbamic Acid Ester Yields on Carbon Dioxide Pressure)

Carbamic acid esters were synthesized in the same manner as in Example 1-6, except that pressure of carbon dioxide was changed, and respective yields of the main product A and the by-product B were calculated. Results thereof are shown in Table 3. The main product A, which was the carbamic acid ester, was obtained with high yields and high selectivity regardless of the pressure of carbon dioxide. The main product A, which was the carbamic acid ester, was obtained with especially high yields and high selectivity, when the pressure of carbon dioxide was 3 to 10 MPa.

TABLE 3

| No. | CO$_2$ Pressure (MPa) | Yield of A (%) | Yield of B (%) |
|---|---|---|---|
| Example 1-21 | 1 | 63 | 5 |
| Example 1-22 | 3 | 84 | 4 |
| Example 1-6 | 5 | 84 | 3 |
| Example 1-23 | 10 | 79 | 2 |
| Example 1-24 | 14 | 57 | 4 |

(Dependency of Carbamic Acid Ester Yields on Solvents)

Carbamic acid esters were synthesized in the same manner as in Example 1-6, except that the solvent was changed, and respective yields of the main product A and the by-product B were calculated. Results thereof are shown in Table 4. The main product A, which was the carbamic acid ester, was obtained with high yields and high selectivity regardless of the kinds of the solvent.

TABLE 4

| No. | Solvent | Yield of A (%) | Yield of B (%) |
|---|---|---|---|
| Example 1-6 | Acetonitrile | 84 | 3 |
| Example 1-25 | Dioxane | 84 | 1 |
| Example 1-26 | Tetrahydrofuran | 73 | 1 |
| Example 1-27 | Diethyl ether | 55 | 3 |
| Example 1-28 | Hexane | 74 | 9 |

2. Synthesis of Carbamic Acid Ester Using Ionic Liquid (Synthesis of Carbamic Acid Ester)

Into an autoclave having an inner volume of 10 mL and equipped with a stirring device, 0.1 mmol of the ionic liquid show n in Table 5, 1 mmol of aniline, 2 mmol of tetramethoxysilane, which is the alkoxysilane compound, and 3 mL of acetonitrile, which is the solvent, were charged; a carbon dioxide cylinder was connected to the autoclave; and the autoclave was sealed. While stirring the inside of the autoclave, the inside of the autoclave was filled with carbon dioxide, temperature was increased to 150° C., the inner pressure of the autoclave was adjusted so as to be 5 MPa, and the reaction was conducted for 24 hours to synthesize the carbamic acid ester (the following chemical equation). After completion of the reaction, the inside of the autoclave was cooled, and remaining carbon dioxide was released.

[Formula 4]

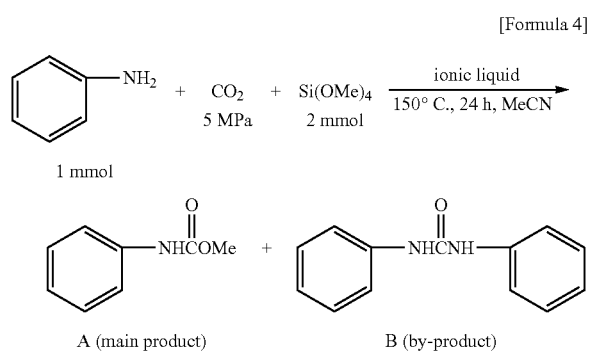

Next, the reaction product was analyzed by liquid chromatography using toluene. Then, respective yields of the main product A and the by-product B were calculated based on aniline. Results thereof are shown in Table 1. Note that the reaction in Comparative Example 2 did not use the ionic acid. In each Example, the main product A, which was the carbamic acid ester, was obtained with a high yield and high selectivity. On the other hand, very little of the carbamic acid ester was obtained in Comparative Example 2.

TABLE 51

| No. | Ionic liquid | Yield of A (%) | Yield of B (%) |
|---|---|---|---|
| Example 2-1 | [DBUH][OAc] | 96 | 3 |
| Example 2-2 | [DBUH][CF$_3$COO] | 93 | 5 |
| Example 2-3 | [DBUH][CF$_3$CH$_2$O] | 96 | 3 |
| Example 2-4 | [DBNH][OAc] | 67 | 3 |
| Example 2-5 | [TBDH][OAc] | 92 | 3 |
| Example 2-6 | [TMGH][OAc] | 25 | 14 |
| Example 2-7 | [C$_4$DABCO][OAc] | 27 | 18 |
| Comparative Example 2 | Not used | 1 | 2 |

(Dependency of Carbamic Acid Ester Yields on Reaction Temperature and Reaction Time)

Carbamic acid esters were synthesized in the same manner as in Example 2-1, except that reaction temperature and reaction time were changed, and respective yields of the main product A and the by-product B were calculated. Results thereof are shown in Table 6. The main product A, which was the carbamic acid ester, was obtained with yields of 45% or higher over the reaction time of 4 hours or more when the reaction temperature was 150° C. or over the reaction time of 1 hour or more when the reaction temperature was 180° C.

TABLE 6

| No. | Reaction temperature (° C.) | Reaction time (h) | Yield of A (%) | Yield of B (%) |
|---|---|---|---|---|
| Example 2-8 | 120 | 15 | 15 | 13 |
| Example 2-9 | 120 | 24 | 25 | 15 |
| Example 2-10 | 150 | 2 | 28 | 7 |
| Example 2-11 | 150 | 4 | 45 | 13 |
| Example 2-12 | 150 | 7 | 69 | 9 |
| Example 2-13 | 150 | 15 | 88 | 4 |
| Example 2-1 | 150 | 24 | 96 | 3 |
| Example 2-14 | 180 | 1 | 47 | 9 |
| Example 2-15 | 180 | 2 | 77 | 6 |
| Example 2-16 | 180 | 4 | 87 | 5 |
| Example 2-17 | 180 | 15 | 80 | 5 |
| Example 2-18 | 180 | 24 | 78 | 5 |

(Dependency of Carbamic Acid Ester Yields on Carbon Dioxide Pressure)

Carbamic acid esters were synthesized in the same manner as in Example 2-1, except that pressure of carbon dioxide was changed, and respective yields of the main product A and the by-product B were calculated. Results thereof are shown in Table 7. The main product A, which was the carbamic acid ester, was obtained with high yields and high selectivity regardless of the pressure of carbon dioxide. The main product A, which was the carbamic acid ester, was obtained with especially high yields and high selectivity, when the pressure of carbon dioxide was 3 to 5 MPa.

TABLE 7

| No. | CO$_2$ Pressure (MPa) | Yield of A (%) | Yield of B (%) |
|---|---|---|---|
| Example 2-19 | 1 | 75 | 7 |
| Example 2-20 | 3 | 94 | 4 |
| Example 2-1 | 5 | 96 | 3 |

(Dependency of Carbamic Acid Ester Yields on Solvents)

Carbamic acid esters were synthesized in the same manner as in Example 2-1, except that the solvent was changed, and respective yields of the main product A and the by-product B were calculated. Results thereof are shown in Table 8. The main product A, which was the carbamic acid ester, was obtained with high yields and high selectivity regardless of the kinds of the solvent.

TABLE 8

| No. | Solvent | Yield of A (%) | Yield of B (%) |
|---|---|---|---|
| Example 2-1 | Acetonitrile | 95 | 3 |
| Example 2-21 | Dioxane | 55 | 4 |
| Example 2-22 | Tetrahydrofuran | 55 | 7 |
| Example 2-23 | Diethyl ether | 43 | 1 |
| Example 2-24 | Hexane | 69 | 1 |

3. Synthesis of Carbamic Acid Ester Using Alkali Metal Compound Catalyst

Into an autoclave having an inner volume of 10 mL and equipped with a stirring device, 0.02 mmol of the alkali metal compound shown in Table 9, 1 mmol of aniline, 2 mmol of tetramethoxysilane, which is the alkoxysilane compound, and 3 mL of acetonitrile, which is the solvent, were charged; a carbon dioxide cylinder was connected to the autoclave; and the autoclave was sealed. While stirring the inside of the autoclave, the inside of the autoclave was filled with carbon dioxide, the temperature was increased to 150° C., the inner pressure of the autoclave was adjusted so as to be 5 MPa, and the reaction was conducted for 24 hours to synthesize the carbamic acid ester (the following chemical equation). After completion of the reaction, the inside of the autoclave was cooled, and remaining carbon dioxide was released.

[Formula 5]

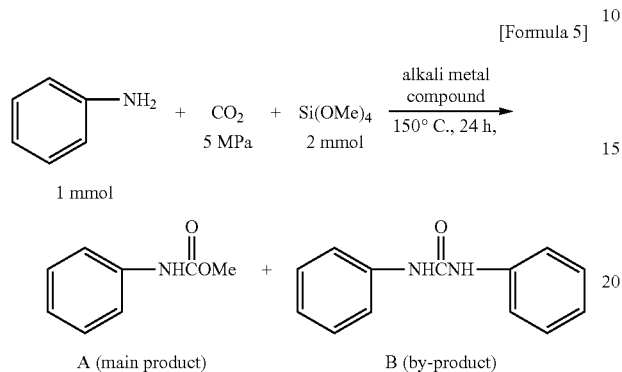

A (main product)    B (by-product)

Next, the reaction product was analyzed by liquid chromatography using toluene. Then, respective yields of the main product A and the by-product B were calculated based on aniline. Results thereof are shown in Table 9. Note that Comparative Example 3 was a reaction not using the alkali metal compound. In each Example, the main product A, which was the carbamic acid ester, was obtained with a high yield and high selectivity. On the other hand, very little of the carbamic acid ester was obtained in Comparative Example 3.

TABLE 9

| No. | Alkali metal compound | Yield of A (%) | Yield of B (%) |
| --- | --- | --- | --- |
| Example 3-1 | K(OAc) | 83 | 8 |
| Example 3-2 | Rb(OAc) | 80 | 7 |
| Example 3-3 | Cs(OAc) | 64 | 3 |
| Example 3-4 | $K_2CO_3$ | 89 | 7 |
| Example 3-5 | $Rb_2CO_2$ | 73 | 10 |
| Example 3-6 | $Cs_2CO_3$ | 81 | 13 |
| Example 3-7 | $KHCO_3$ | 84 | 16 |
| Example 3-8 | KOH | 76 | 11 |
| Example 3-9 | $KO^tBu$ | 87 | 12 |
| Comparative Example 3 | Not used | 1 | 2 |

In addition, different carbamic acid esters were synthesized in the same manner as in Example 3-4 (the following chemical equation). The types and yields of the main products obtained are shown together below. It has been shown that extremely inexpensive potassium compounds are usable for the catalyst.

[Formula 6]

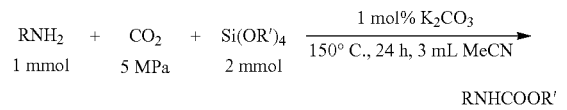

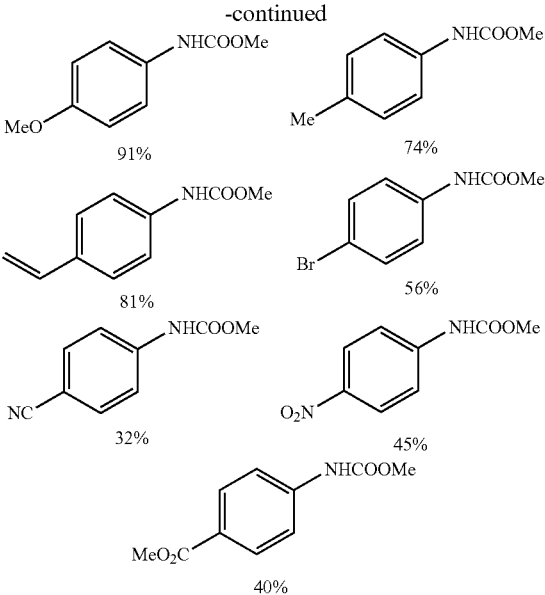

Moreover, urethane was synthesized from each of 2,4-toluenediamine (TDA) and 4,4'-diaminodiphenylmethane (MDA) in the same manner as in Example 3-3 (the following chemical equation). The types and yields of the main products obtained are shown together below.

[Formula 7]

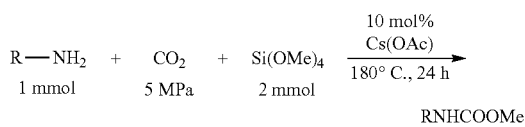

from TDA

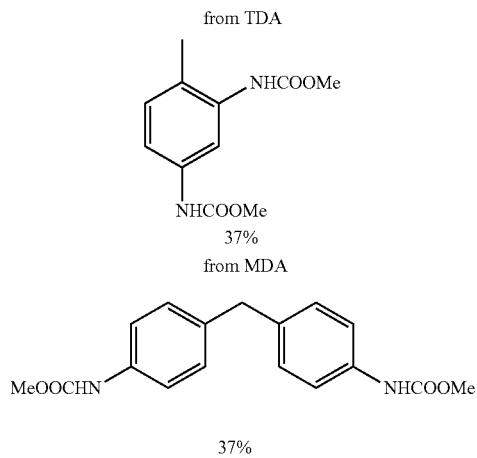

The invention claimed is:

1. A method of producing a carbamic acid ester, comprising:
reacting an amine, carbon dioxide, and an alkoxysilane compound in the presence of a catalyst containing a zinc compound.

2. The method according to claim 1, wherein the zinc compound is at least one of zinc oxide, a zinc halide, zinc trifluoromethanesulfonate, and zinc acetate.

3. The method according to claim 1, wherein the catalyst further contains a ligand.

4. The method according to claim 3, wherein the zinc compound is zinc acetate, and the ligand is at least one of 1,10-phenanthroline, 2,2'-bipyridine, N,N'-bis(2-pyridylmethyl)ethylenediamine, and 1,4,8,11-tetraazacyclotetradecane.

5. The method according to claim 1, wherein the amine, the carbon dioxide, and the alkoxysilane compound are reacted at a pressure of the carbon dioxide of 3 to 10 MPa.

6. A method of producing a carbamic acid ester, comprising:
reacting an amine, carbon dioxide, and an alkoxysilane compound in the presence of an ionic liquid.

7. The method according to claim 6, wherein an anion of the ionic liquid is at least one of an acetate ion, a trifluoroacetate ion, and a 2,2,2-trifluoroethanol ion.

8. The method according to claim 6, wherein a cation of the ionic liquid is at least one of the compounds represented by the following formulas (1) to (5):

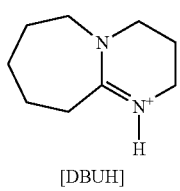

(1)

[DBUH]

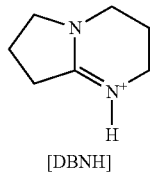

(2)

[DBNH]

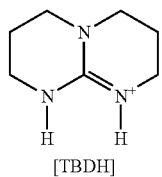

(3)

[TBDH]

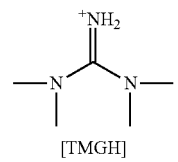

(4)

[TMGH]

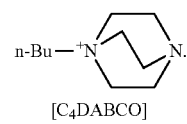

(5)

[C4DABCO]

9. The method according to claim 8, wherein the cation of the ionic liquid is at least one of the compounds represented by the formulas (1) and (2), and the anion of the ionic liquid is acetate ion.

10. The method of according to claim 6, wherein the amine, the carbon dioxide, and the alkoxysilane compound are reacted at a pressure of the carbon dioxide of 3 to 5 MPa.

11. A method of producing a carbamic acid ester, comprising:
reacting an amine, carbon dioxide, and an alkoxysilane compound in the presence of a catalyst containing an alkali metal compound.

12. The method according to claim 11, wherein the alkali metal compound is at least one of a potassium compound, a rubidium compound, and a cesium compound.

13. The method according to claim 11, wherein the alkali metal compound is at least one of rubidium acetate, cesium acetate, rubidium carbonate, and cesium carbonate.

14. The method according to claim 11, wherein the alkali metal compound is at least one of potassium acetate, potassium carbonate, potassium hydrogen carbonate, potassium hydroxide, and potassium tert-butoxide.

15. The method according to claim 1, wherein the alkoxysilane compound is a tetraalkoxysilane.

16. The method according to claim 15, wherein the tetraalkoxysilane is tetramethoxysilane.

17. The method according to claim 1, wherein the amine, the carbon dioxide, and the alkoxysilane compound are reacted at a temperature of 150 to 180° C.

* * * * *

UNITED STATES PATENT AND TRADEMARK OFFICE
CERTIFICATE OF CORRECTION

PATENT NO. : 10,752,579 B2
APPLICATION NO. : 16/328530
DATED : August 25, 2020
INVENTOR(S) : Choi et al.

Page 1 of 1

It is certified that error appears in the above-identified patent and that said Letters Patent is hereby corrected as shown below:

On the Title Page

Item (71) Applicant: Please correct "Ibaraki, Japan" to read -- Tokyo, Japan --

In the Specification

Column 11, Line 1: Please correct "show n" to read -- shown --

Signed and Sealed this
Sixth Day of October, 2020

Andrei Iancu
*Director of the United States Patent and Trademark Office*